(12) United States Patent
Wang

(10) Patent No.: US 7,527,737 B2
(45) Date of Patent: May 5, 2009

(54) HEMODIALYSIS APPARATUS AND METHODS

(76) Inventor: Xiangyu Wang, Room 12C, 8 Building, Seamark Greatcity, Nanshan District, Shenzhen (CN) 518054

( * ) Notice: Subject to any disclaimer, the term of this patent is extended or adjusted under 35 U.S.C. 154(b) by 457 days.

(21) Appl. No.: 11/382,307

(22) Filed: May 9, 2006

(65) Prior Publication Data
US 2007/0262020 A1   Nov. 15, 2007

(51) Int. Cl.
*B01D 61/00* (2006.01)
*A61M 1/36* (2006.01)
(52) U.S. Cl. .................. 210/646; 210/695; 210/748; 210/223; 210/243; 210/321.6; 604/5.01; 604/6.08
(58) Field of Classification Search ............. 604/5.01, 604/6.48; 210/646, 748, 223, 243, 321.6, 210/695
See application file for complete search history.

(56) References Cited

U.S. PATENT DOCUMENTS

| 4,181,610 A | 1/1980 | Shintani et al. |
| 2005/0015040 A1 | 1/2005 | Wuepper |

FOREIGN PATENT DOCUMENTS

| DE | 4018416 A1 | 12/1990 |
| IT | 1170977 | 5/1981 |

*Primary Examiner*—David A Reifsnyder
(74) *Attorney, Agent, or Firm*—Matthias Scholl P.C.; Matthias Scholl

(57) ABSTRACT

A hemodialysis apparatus comprises dialyzer means, dialyzing solution supply means, blood circulation means, and blood irradiation means. Employing electromagnetic radiation in the red visible and near infrared spectrum as part of a hemodialysis apparatus prevents long-term side effects associated with the use of dialysis, including cardiovascular diseases and anemia, and protects and restores the remaining kidney function.

4 Claims, 1 Drawing Sheet

HEMODIALYSIS APPARATUS AND METHODS

BACKGROUND OF THE INVENTION

1. Field of the Invention

This invention related to a hemodialysis apparatus and blood dialysis methods and specifically to an improved hemodialysis apparatus and blood dialysis methods employing electromagnetic radiation, including visible light radiation and near infrared radiation, to purify blood.

2. Description of Related Art

Hemodialysis therapy is an extracorporeal (i.e., outside the body) process which removes toxins and water from a patient's blood. Hemodialysis machines are well known in the art and are described, for example, in U.S. Pat. Nos. 3,598,727, 4,172,033, 4,267,040, and 4,769,134. A hemodialysis machine pumps blood from the patient, through a dialyzer, and then back to the patient. The dialyzer removes the toxins and water from the blood utilizing osmosis, membrane diffusion, and ultrafiltration principles. Typically, a patient with chronic kidney disease requires hemodialysis three times per week for 3-6 hours per session. Removing blood from the body requires a vascular access to the patient's blood system. This vascular access can be accomplished by surgically modifying the patient's own blood vessels or attaching an artificial device to the vessels. If the vascular access site is entirely beneath the skin, the skin and the vascular site must be punctured by a needle attached to blood tubing. This needle and tubing is typically called a "set".

Long-term hemodialysis may result in many complications including worsening of renal anemia, cardiovascular diseases, and loss of the remaining renal function. Conventional hemodialysis machines remove toxins and water from the patient's blood only, but do not address cardiovascular complications or anemia generally resulting from long-term hemodialysis. Specifically, patients undergoing long-term dialysis generally die as a result of cardiovascular complications rather than as a result of kidney failure.

Light-irradiation therapies have been used in medicine. See, e.g., U.S. Pat. Nos. 6,113,566 and 6,951,548. Subjecting blood to ultraviolet light irradiation has been known to kill and eliminate a host of bacterial infections, germs, viruses, and other harmful pathogens and toxins from the body. In addition, exposure of blood to electromagnetic radiation in other regions of the electromagnetic spectrum may have other effects including enhancing the healing of wounds, eliminating free radicals, delaying skin aging, improving skin condition and complexion, reducing blood viscosity, increasing oxygen-carrying capacity of blood, regulating the immune system, and many others.

However, the benefits of light irradiation have not heretofore been employed in connection with hemodialysis so as to lower the risks thereof. Accordingly, much work remains to be done in this area of science and medicine.

BRIEF SUMMARY OF THE INVENTION

In one embodiment of the invention described herein provided is a hemodialysis apparatus comprising dialyzer means, dialyzing solution supply means, blood circulation means, and blood irradiation means.

In a class of the first embodiment, the blood irradiation means comprises one or more electromagnetic sources; and a support means, wherein, one or more of the electromagnetic sources are attached to the frame; and one or more of the electromagnetic sources emit visible or near infrared radiation.

In a subclass of this class, the hemodialysis apparatus comprises more than one electromagnetic source, the electromagnetic sources being distributed annularly with respect to said first circuit and/or said second circuit.

In a second subclass of this class, the first circuit and/or the said second circuit are distributed annularly with respect to one or more of the electromagnetic sources.

In a third subclass of this class, one or more of the electromagnetic sources are disposed within the first circuit and/or the second circuit.

In a second class of the first embodiment, one or more of the electromagnetic sources emit radiation of single, multiple, or continuous wavelengths.

In a third class of the first embodiment, one or more of the electromagnetic sources emit radiation at one or more wavelengths between about 500 nm and about 850 nm.

In a fourth class of the first embodiment, the hemodialysis apparatus is used for prevention and treatment of cardiovascular diseases or anemia, or for prevention of further loss of kidney function in patients suffering from a partial loss of kidney function.

In a fifth class of the first embodiment, the blood circulation means comprises a first circuit for drawing blood from a patient and delivering blood to the dialyzer means, and a second circuit for returning dialyzed blood back to a patient; and the blood irradiation means irradiates blood present in the first circuit, blood present in the second circuit, or blood present both in the first circuit and in the second circuit.

In a subclass of this class, blood irradiation means comprises one or more electromagnetic sources; and support means; wherein, one or more of the electromagnetic sources are attached to the support means; and one or more of the electromagnetic sources emit visible or near infrared radiation.

In a subclass of this class, the hemodialysis apparatus comprises more than one electromagnetic source, the electromagnetic sources being distributed annularly with respect to the first circuit and/or the second circuit.

In a subclass of this class, the first circuit and/or the second circuit are distributed annularly with respect to one or more of the electromagnetic sources.

In a subclass of this class, one or more of the electromagnetic sources are disposed within the first and/or the second circuit.

In a sixth class of the first embodiment, one or more of the irradiation sources are selected from the group consisting of: one or more light emitting diodes; one or more incandescent light sources; one or more fluorescent light sources; one or more sodium light sources; one or more halogen light sources; and/or one or more laser radiation sources.

In a seventh class of the first embodiment, the first circuit and the second circuit comprise blood tubing; the support means are configured annularly; the electromagnetic sources are disposed annularly on the support means with respect to the blood tubing.

In a second embodiment of the invention described herein provided is a hemodialysis set for a hemodialysis apparatus comprising a tubing having an outer tubing wall, an inner tubing wall, and one or more electromagnetic sources disposed between said inner tubing wall and said outer tubing wall.

In a third embodiment of the invention described herein provided is a method for purifying blood in a hemodialysis apparatus comprising (i) dialyzing blood and (ii) irradiating blood with visible or near infrared radiation.

BRIEF DESCRIPTION OF THE DRAWINGS

Below, the invention is explained in more detail with reference to drawings, in which.

DETAILED DESCRIPTION OF THE INVENTION

Figure 1:
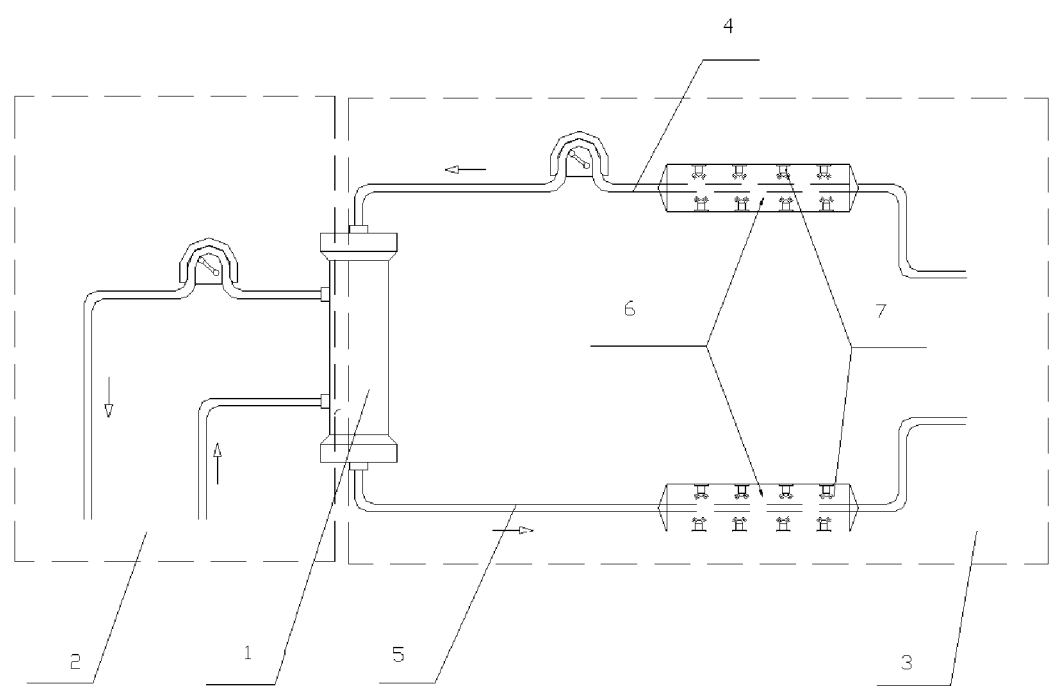
FIG. 1 is a schematic representation of the hemodialysis apparatus of the present invention.

This invention provides a new type of hemodialysis machine, which solves the technological problem that existing hemodialysis machines cannot solve, i.e., to perform the dialysis of blood of a patient to remove metabolites and other poisonous substances, while also treating anemia and cardiovascular complications arising from blood dialysis, as well as preserving or protecting the remaining kidney function.

The technological problem is solved by utilizing the following technological schemes.

A hemodialysis apparatus comprises dialyzer means for blood purification, dialyzing solution supply means for preparing and circulating dialyzate solution, blood circulation means for circulating blood in vitro, and blood irradiation means for irradiating blood with electromagnetic radiation.

The term "dialyzer means," as used herein, refers to a device through which blood and dialysis fluids flow, separated by a semipermeable membrane. Some dialyzers are so small that they can be it held in a hand. Basic types of dialyzers include: the plate and the hollow fiber dialysis. The term "dialyzer means" as used herein includes hemofilters, ultrafilters, and hemodiafilters.

The most essential quality of the dialyzer is the performance, i.e. the efficiency with which it purifies the blood. A further concern is its compatibility, i.e. that the contact between the blood and the foreign materials of the dialyzer does not evoke any clinically important adverse reactions.

The term "dialyzing solution supply means," as used herein, refers to a device which stores and/or mixes and/or pumps a dialyzing solution into the dialyzer means, and includes dialyzer pumps, dialyzer solution storing tanks, and dialyzer solution supply lines.

The term "blood circulation means," as used herein, refers to a device which circulates blood in vitro, and includes blood pumps (e.g., peristaltic blood pumps).

The term "cardiovascular diseases," as used herein, refers to a class of diseases that involve the heart and/or blood vessels (arteries and veins), including but not limited to atherosclerosis, vasculitis, coronary heart disease, stenosis, cardiac ischemia, angina pectoris, myocardial infarction, and congestive heart failure.

The term "anemia," as used herein, refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

The terms "disorders," "diseases," and "conditions" are used inclusively and refer to any condition deviating from normal.

The blood irradiation means is provided to prevent and treat cardiovascular diseases, to treat anemia, and to preserve and protect the remaining kidney function. The light sources of the blood irradiation means emit electromagnetic waves of various wavelengths to illuminate and treat the blood in a blood circulation system in vitro.

In certain embodiments, blood circulation means comprises an artery-blood circuit for drawing blood from an artery of a patient, and a vein-blood circuit for returning dialyzed blood to a patent's vein.

As used herein, the terms "circuit" and "extracorporeal circuit" refer to any part of a system for carrying a patient's blood outside of the patient's body for the purpose of blood purification and/or any system that is inserted into human body for the purpose of blood purification. A circuit is comprised, e.g., of plastic tubes or other types of tubes for carrying a patient's blood.

In certain embodiments, blood of a patient may be drawn out from an artery of the patient and returned, after purification, into a vein of the patient. In this embodiment, the part of the circuit which carries blood before it is purified is referred to as "artery-blood circuit" and the part of the circuit which carriers blood after it is purified is referred to as "vein-blood circuit".

The term "blood irradiation means," as used herein, refers to a device used to irradiate blood with electromagnetic radiation.

The term "support means," as used herein, refers to any physical part to which electromagnetic sources are attached. The role of the support means is to provide attachment point for electromagnetic sources so as to distribute radiation sources spatially with respect to the blood circuit and to focus and distribute (in certain embodiments evenly) the electromagnetic waves onto the blood circuit.

In certain embodiments, blood irradiation means irradiates blood in the artery-blood circuit, in the vein-blood circuit, or in both the artery-blood circuit and the vein-blood circuit at the same time.

The terms "electromagnetic sources," "irradiation sources," and "light sources" as used herein, refer to sources of electromagnetic radiation.

In certain embodiments, the irradiation sources are selected from the group consisting of light emitting diodes; incandescent light sources; fluorescent light sources; sodium light sources; halogen light sources; and/or laser radiation sources. Suitable filters may be used. Among the sources that can be used are without limitation quartz, halogen and arc lamp sources, gold vapor, tunable argon-pump dye laser or copper vapor-pumped dye laser or Nd:YAG-pumped dye laser or other wavelength-specific lasers, and standard visible light sources in general.

The electromagnetic radiation sources of the blood irradiation means are able to emit radiation of various wavelengths and powers as necessary to practice the embodiments of the present invention.

In certain embodiments, the irradiation sources emit electromagnetic radiation in the visible spectrum and/or near infrared spectrum, and particularly electromagnetic radiation with wavelengths of from about 500 nm to about 850 nm. In one class, the electromagnetic sources emit visible red light. The emitted radiation is of a single wavelength, (e.g., 825 nm, or 775 nm, or 750 nm), or of multiple wavelengths (e.g., 825 nm, and 775 nm, and 750 nm), or of a continuous range of wavelengths (e.g., each wavelength continually from 750 to 825 nm), or of a multiple continuous wavelengths (e.g., each wavelength continually from 750 to 775 nm and each wavelength continually from 800 to 825 nm).

The emitted radiation can be of various intensity as necessary to accomplish prevention and treatment of cardiovascular diseases or anemia or prevention of further loss of kidney function in patients suffering from a partial loss of kidney function. Particularly, the intensity of the emitted radiation is of between 0 lux and 50,000 lux, and more particularly between 500 and 10,000 lux.

In certain embodiments of the present invention, electromagnetic sources are distributed spatially around the portion of a blood circuit which is subjected to electromagnetic radiation. For example, if the irradiated portion of a blood circuit is a cylindrical tubing, then the light sources are disposed on a cylindrical surface having a diameter larger than the diameter of the tubing; alternatively, the light sources are disposed directly within the cylindrical tubing and may or may not come into contact with blood directly. In certain embodiments, the irradiated portion of a blood circuit which is a cylindrical tubing is arranged into a helical coil, having a hollow inner passage way that extends the entire way of the coil. The electromagnetic sources are distributed inside the inner passage and/or outside the coil on a cylindrical surface having a diameter larger than the diameter of the coil. In certain embodiments, each coil turn can be irradiated by a plurality electromagnetic sources arranged annularly.

Other spatial arrangements are possible and generally, the light sources are distributed spatially with respect to the irradiated portion of the blood circuit so as to distribute the electromagnetic radiation evenly within the circuit(s) to be irradiated and/or to provide the appropriate amount of electromagnetic radiation so as to accomplish prevention and treatment of cardiovascular diseases or anemia or prevention of further loss of kidney function in patients suffering from a partial loss of kidney function.

In certain embodiments, blood irradiation leads to increased secretion of erythropoietin (EPO) which helps to relieve anemia. Blood irradiation also reduces the number of free radicals, including oxygen free radicals, which helps to decrease the occurrence of cardiovascular diseases. Light illumination therapy also helps to protect the remaining kidney function in blood dialysis patients.

With reference to FIG. 1, a hemodialysis apparatus comprises dialyzer means for blood purification 1, dialyzing solution supply means for preparing and circulating dialysate 2, blood circulation means for circulating blood in vitro 3, and blood irradiation means for irradiating blood with electromagnetic radiation 6.

Blood circulation means for circulating blood in vitro 3 comprises an artery-blood circuit 4 which carries blood drawn out from a patient, and a vein-blood circuit 5 which returns purified blood back to a patient.

Blood irradiation means 6 comprises a plurality of electromagnetic radiation sources 7, which illuminate blood in the artery-blood circuit 4 and/or vein-blood circuit 5. The electromagnetic sources 7 of the blood irradiation means 6 provide electromagnetic radiation in a continuous rage of wavelengths between 500 nm-850 nm (integrated tungsten/halogen light source). The electromagnetic sources 7 are attached to two cylindrically shaped support frames each of which has an inner passage way. The passage way of one of the support frames encloses the artery-blood circuit; the passage way of the other support frame encloses the vein-blood circuit. The axis of rotation of a support frame coincides with the axis of rotation of a circuit.

Light-illumination therapy may be performed at any stage of blood circulation, including sections of blood circulation both in vivo and in vitro. Generally because of the increased risk of trauma and infection when performing blood irradiation in vivo, we adopt the safe way of illumination in vitro.

Additionally, blood irradiation means may be set up as part the hemodialysis apparatus, or it may be used independently from a hemodialysis apparatus. The efficiency of the blood irradiation apparatus used independently from a hemodialysis apparatus is lower than its efficiency when used with the hemodialysis apparatus.

The terms "hemodialysis set" and "set," as used herein, refer to blood tubing and one or more needles used to provide a connection between a vascular access site of a patient and a dialysis machine. In certain embodiments of the invention described herein, the blood tubing of a hemodialysis set is made of plastic material and has an outer tubing wall and an inner tubing wall. One or more electromagnetic sources may be disposed between the inner tubing wall and the outer tubing wall. Alternatively, support means is provided and encloses the tubing, and to the support is attached a plurality of electromagnetic sources.

In other aspects the invention provides methods for preventing cardiovascular complications or anemia generally resulting from long-term hemodialysis. These methods include in addition to dialyzing blood irradiating blood with visible or near infrared radiation. The radiation and apparatus employed in these methods are as elsewhere described herein.

This invention is not to be limited to the specific embodiments disclosed herein and modifications for various applications and other embodiments are intended to be included within the scope of the appended claims. While this invention has been described in connection with particular examples thereof, the true scope of the invention should not be so limited since other modifications will become apparent to the skilled practitioner upon a study of the drawings, specification, and following claims.

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

What is claimed is:

1. A hemadialysis apparatus comprising:
   dialyzer means;
   dialyzing solution supply means;
   blood circulation means;
   blood irradiation means comprising a plurality of electromagnetic sources; wherein
   said electromagnetic sources are evenly and annularly distributed around said blood circulation means whereby delivering uniform electromagnetic intensity; and
   said electromagnetic sources emit near infrared radiation.

2. The hemadialysis apparatus of claim 1 wherein said electromagnetic sources emit radiation of single, multiple or continuous wavelengths.

3. A method for preventing cardiovascular complication or anemia generally resulting from long-term hemodialysis comprising: (1) dialyzing blood; and (2) irradiating blood with near infrared radiation; steps (1) and (2) being performed simultaneously with the hemodialysis apparatus of claim 1.

4. The method of claim 3, wherein the method also prevents a further loss of kidney function in patients suffering from a partial loss of kidney function.

* * * * *